(12) United States Patent
Albert et al.

(10) Patent No.: US 6,264,614 B1
(45) Date of Patent: Jul. 24, 2001

(54) SYSTEM AND METHOD FOR GENERATING AND TRANSFERRING MEDICAL DATA

(75) Inventors: David E. Albert; Carl J. Rieger, both of Oklahoma City; Mac L. Reiter, Stillwater, all of OK (US); Rik Slaven, Bellevue, WA (US)

(73) Assignee: Data Critical Corporation, Bothell, WA (US)

( * ) Notice: Subject to any disclaimer, the term of this patent is extended or adjusted under 35 U.S.C. 154(b) by 0 days.

(21) Appl. No.: 09/387,013

(22) Filed: Aug. 31, 1999

(51) Int. Cl.[7] .................................................. A61B 5/00
(52) U.S. Cl. ........................ 600/528; 128/904; 600/514
(58) Field of Search .................................... 600/528, 514; 128/903, 904

(56) References Cited

U.S. PATENT DOCUMENTS

| | | | |
|---|---|---|---|
| 3,717,857 | 2/1973 | Evans | 340/177 R |
| 3,731,311 | 5/1973 | Williams | 343/17.2 PC |
| 3,768,014 | 10/1973 | Smith et al. | 324/158 R |
| 3,782,367 | 1/1974 | Hochberg et al. | 128/2.06 A |
| 3,882,277 | 5/1975 | DePedro et al. | 179/2 DP |
| 3,885,552 | 5/1975 | Kennedy | 128/2.05 R |
| 3,898,984 | 8/1975 | Mandel et al. | 128/2.1 A |
| 3,909,599 | 9/1975 | Trott, Jr. et al. | 235/151.3 |
| 4,027,146 | 5/1977 | Gilmore | 235/151.31 |
| 4,083,366 | 4/1978 | Gombrich et al. | 128/2.05 T |
| 4,095,050 | 6/1978 | Beachem et al. | 179/2 A |
| 4,250,888 | 2/1981 | Grosskopf | 128/702 |
| 4,281,664 | 8/1981 | Duggan | 128/696 |

(List continued on next page.)

FOREIGN PATENT DOCUMENTS

| | | | |
|---|---|---|---|
| 675675 A5 | 10/1990 | (CH) | A61B/5/04 |
| 2181554 | 4/1987 | (GB) | A61B/5/04 |
| WO 90/08361 | 7/1990 | (WO) | A61B/5/04 |
| WO 92/06551 | 4/1992 | (WO) | H04M/11/04 |

OTHER PUBLICATIONS

B. P. Lahti, "Modern Digital and Analog Commincation Systems," 8 pp. (including pp. 619–623), Holt, Rinehart and Winston, New York, New York (1983).

W. H. Chang et al., "A New Data Compression Algorithm for Computerized ECG Signal," pp. 311–314, IEEE/Eighth Annual Conference of the Engineering in Medicine and Biology Society (1986).

T. C. Bartee, "Data Communications, Networks, and Systems," 8 pp. (including pp. 364–369), SAMS, Division of Prentice Hall Computer Publishing (1991).

Primary Examiner—Carl H. Layno
(74) Attorney, Agent, or Firm—McAfee & Taft

(57) ABSTRACT

A computer site includes a data generating source. The source may include a device (e.g. a heart monitor) which may be manipulated by the patient to sense a biological function or condition such as a heart beat. The device outputs an audible signal in response to the monitored condition. A computer that can be operated by the patient or other initial user at the site runs a program that processes an electric signal generated in response to the audible signal as received through a microphone connected to the computer. The program is downloaded or otherwise accessed through a computer communications network (e.g. Internet). The computer sends resulting data signals over this network. Using a plurality of the foregoing components, any number of patients (or other users) that can access the computer communications network can provide real-time information about their personal medical condition (or other generated data) to their personal medical care providers (or other remote end users).

37 Claims, 7 Drawing Sheets

Microfiche Appendix Included
(2 Microfiche, 72 Pages)

U.S. PATENT DOCUMENTS

| | | | |
|---|---|---|---|
| 4,319,241 | 3/1982 | Mount | 340/870.38 |
| 4,409,984 | 10/1983 | Dick | 128/696 |
| 4,428,381 | 1/1984 | Hepp | 128/715 |
| 4,449,536 | 5/1984 | Weaver | 128/696 |
| 4,458,693 | 7/1984 | Badzinski et al. | 128/715 |
| 4,531,527 | 7/1985 | Reinhold, Jr. et al. | 128/696 |
| 4,567,883 | 2/1986 | Langer et al. | 128/696 |
| 4,596,900 | 6/1986 | Jackson | 179/2 A |
| 4,660,032 | 4/1987 | Tsunoda | 340/825.44 |
| 4,745,408 | 5/1988 | Nagata et al. | 340/825.44 |
| 4,791,933 | 12/1988 | Asai et al. | 128/640 |
| 4,802,222 | 1/1989 | Weaver | 381/35 |
| 4,803,625 | 2/1989 | Fu et al. | 364/413.03 |
| 4,838,275 | 6/1989 | Lee | 128/670 |
| 4,883,064 | 11/1989 | Olson et al. | 128/696 |
| 4,889,134 | 12/1989 | Greenwold et al. | 128/696 |
| 4,938,229 | 7/1990 | Bergelson et al. | 128/696 |
| 4,974,607 | 12/1990 | Miwa | 128/904 |
| 4,981,141 | 1/1991 | Segalowitz | 128/696 |
| 5,012,411 | 4/1991 | Policastro et al. | 364/413.06 |
| 5,023,906 | 6/1991 | Novas | 379/372 |
| 5,036,869 | 8/1991 | Inahara | 128/903 |
| 5,043,721 | 8/1991 | May | 340/825.44 |
| 5,050,612 | 9/1991 | Matsumura | 128/670 |
| 5,078,134 | 1/1992 | Heilman et al. | 128/421 |
| 5,113,869 | 5/1992 | Nappholz et al. | 128/696 |
| 5,146,216 | 9/1992 | DeLuca et al. | 340/825.52 |
| 5,172,698 | 12/1992 | Stanko | 128/697 |
| 5,191,891 | 3/1993 | Righter | 128/710 |
| 5,223,831 | 6/1993 | Kung et al. | 340/825.44 |
| 5,224,485 | 7/1993 | Powers et al. | 128/696 |
| 5,226,431 | 7/1993 | Bible et al. | 128/904 |
| 5,285,496 | 2/1994 | Frank et al. | 380/9 |
| 5,293,484 | 3/1994 | Dabbs, III et al. | 395/164 |
| 5,302,947 | 4/1994 | Fuller et al. | 340/825.34 |
| 5,307,263 | 4/1994 | Brown | 364/413.09 |
| 5,307,818 | 5/1994 | Segalowitz | 128/696 |
| 5,319,355 | 6/1994 | Russek | 340/573 |
| 5,321,618 | 6/1994 | Gessman | 364/413.06 |
| 5,333,615 | 8/1994 | Craelius et al. | 128/696 |
| 5,333,616 | 8/1994 | Mills et al. | 128/696 |
| 5,336,245 | 8/1994 | Adams et al. | 607/32 |
| 5,337,044 | 8/1994 | Folger et al. | 340/825.44 |
| 5,339,824 | 8/1994 | Engira | 128/712 |
| 5,347,268 | 9/1994 | Nelson et al. | 340/825.44 |
| 5,365,935 | 11/1994 | Righter et al. | 128/710 |
| 5,433,736 | 7/1995 | Nilsson | 607/59 |
| 5,446,678 | 8/1995 | Saltzstein et al. | 364/514 R |
| 5,452,356 | 9/1995 | Albert | 380/9 |
| 5,465,727 | 11/1995 | Reinhold, Jr. | 128/710 |
| 5,466,246 | 11/1995 | Silvian | 607/32 |
| 5,481,255 | 1/1996 | Albert et al. | 340/825.55 |
| 5,503,158 | 4/1996 | Coppock et al. | 128/696 |
| 5,544,661 | 8/1996 | Davis et al. | 128/700 |
| 5,735,285 | 4/1998 | Albert et al. | 128/696 |
| 5,997,476 * | 12/1999 | Brown | 600/300 |
| 6,022,315 * | 2/2000 | Lliff | 600/300 |
| 6,090,056 * | 7/2000 | Bystrom et al. | 601/41 |
| 6,095,985 * | 8/2000 | Raymond et al. | 600/513 |

* cited by examiner

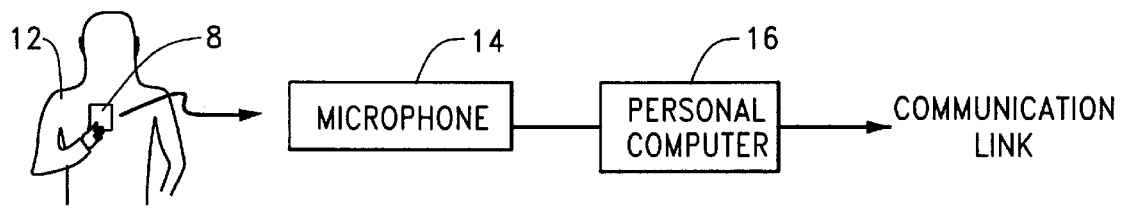
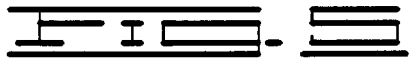
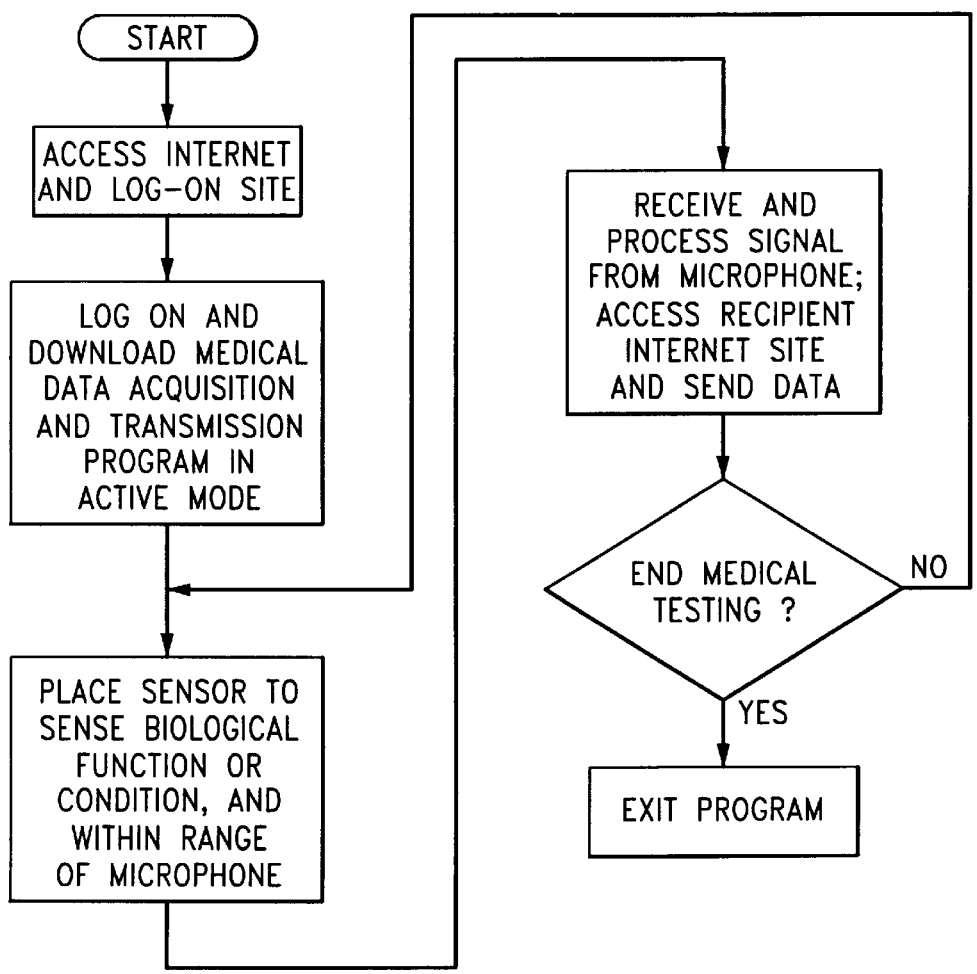
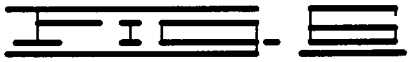

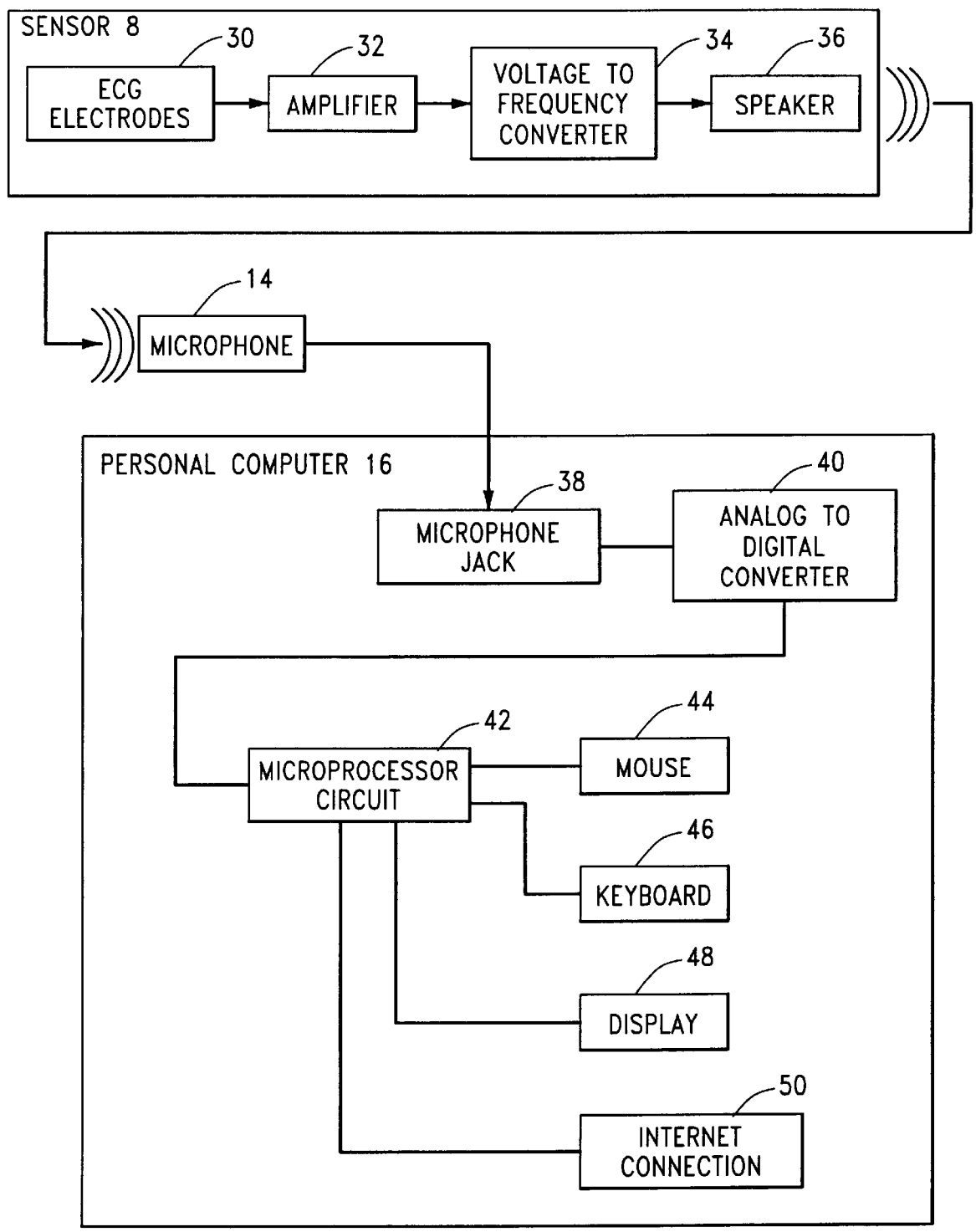
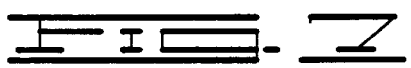

SYSTEM AND METHOD FOR GENERATING AND TRANSFERRING MEDICAL DATA

This specification contains a microfiche appendix consisting of two microfiche sheets having 72 frames of computer program listings.

BACKGROUND OF THE INVENTION

This invention relates generally to systems and methods for generating and transferring medical and other data. A specific implementation includes a remote heart monitoring method.

Many industries use real-time information, but the medical field is one in which such information is particularly critical. In hospitals, for example, patients may have their biological functions or conditions continuously monitored so that any significant change can be immediately detected and addressed by appropriate personnel. Such monitoring includes generating the information and transferring it to where it is to be used.

U.S. Pat. No. 5,481,255 to Albert et al. discloses transmitting medical data, for example, through a paging network to a pager receiver connected to a computer, such as a palmtop computer held by a physician. In one example, a patient is connected to an electrocardiogram (ECG) machine to generate ECG information that is processed and transmitted through the paging network to the receiver and attached computer.

U.S. Pat. No. 5,735,285 to Albert et al. discloses another communication system for conveying ECG data or other biomedical waveform data between a patient and an attending physician's location. The patient employs a HEART CARD™ device from Instromedix, Inc., or the like, which converts the patient's ECG signal into a frequency modulated audio signal that may then be analyzed by audio inputting via a telephone system to a selected hand-held computer device with integrated microphone and audio system. The computer device functions to digitize, record and demodulate the frequency modulated signal for presentation and viewing on the hand-held computer. The audio signal can also be input directly into a personal computer (PC) via a standard personal computer microphone. The audio signal can be input directly into a PC through a phone line connection via a standard "voice-capable" modem, for example. The stored ECG audio signal can be retransmitted via telephone, either wireline or wireless. At a receiving end, a programmed hand-held computer can be used to receive the audio FM biomedical signal for digitization, recording and demodulation for viewing. Such computer can be one with integrated microphone, audio analog to digital converter, digital to analog converter, speaker, and central processing unit with memory for performing various computational, data storage and signal processing tasks.

Despite previously disclosed or implemented systems, there is still the need for a novel and improved system and method for generating and transferring medical (or other) data, especially a system and method which enable a patient to communicate with a medical care provider in real time virtually from anywhere. Preferably such a system and method should be able to communicate globally, such as via the Internet. Such a system and method should be inexpensive, simple, and easy-to-use. This includes use of a computer without having to purchase or manually install a specialized computer application program or any special hardware. Such system and method should be relatively inexpensive both for the patient or other input user and the medical care provider or other recipient to use (e.g., minimal equipment requirements, no long distance telephone tolls). Such system and method should quickly (ideally, in real time) provide accurate data from the input user to the recipient.

SUMMARY OF THE INVENTION

The present invention meets the aforementioned needs by providing a novel and improved system and method for generating and transferring medical and other data. For example, the system and method permit the monitoring of biological functions and conditions of a plurality of patients and the reporting of the resulting data to respective medical care providers. In a particular implementation, the present invention provides for remote heart monitoring.

In a preferred embodiment, a device that can be manipulated by a patient senses some function or condition of the patient. One example is a small, inexpensive, hand-held heart monitor that a patient can hold against his or her chest; when used, the device outputs an audible signal responsive to the beating of the heart, such as the electrocardiogram. A computer that can be operated by the patient runs a program that processes an electric signal generated in response to the audible signal as received through a microphone connected to the computer. The computer can send resulting data signals over a computer communication network and preferably over a global communication network such as the Internet. Using a plurality of the foregoing components, any number of patients that can access the computer communication network can quickly, easily, inexpensively, and accurately provide real-time information about their personal medical condition to their personal medical care providers. The real-time information can also be used locally such as by the individual during exercise or simply while trying to monitor or modulate the sensed condition (e.g., to lower heart rate, blood pressure, or stress).

One definition of the system for generating and transferring medical data of the present invention comprises: means for sensing a biological function or condition; and means, communicating with the means for sensing, for transferring a response to the sensed biological function or condition over the Internet.

In accordance with another definition of the present invention, the system comprises a sensor used by a human user to sense a function or condition of the user's body. It also comprises a personal computer located with the sensor. The personal computer has a microphone connector and analog to digital conversion means which are communicated with the sensor such that a digital processing circuit of the personal computer receives from the analog to digital conversion means a digital electric signal derived from an analog electric signal received through the microphone connector in response to the user's body function or condition sensed by the sensor. The personal computer is programmed to transfer data representative of the received digital electric signal over a computer communication network contemporaneously with the sensor sensing the user's body function or condition. This system can further comprise a recipient computer located at a medical facility and connected to communicate with the computer communication network, wherein the recipient computer is programmed to receive the data transferred over the computer communication network and to provide a visible representation of the sensed body function or condition and to store the data in a searchable database. The system can comprise a recipient computer located at a data communication service provider facility and connected to communicate with the computer communication network, wherein the recipient computer is programmed to receive the data transferred over the computer communication network and to transmit in response thereto another signal to an end user.

Still another definition of the present invention for a system for generating and transferring medical data comprises: a sensor to provide an acoustical signal in simultaneous response to a biological function or condition; a microphone, located with the sensor, to receive the acoustical signal as the acoustical signal is provided from the sensor; and a computer connected to the microphone and adapted to transfer over the Internet, in real-time response to the microphone receiving the acoustical signal, electric signals representative of the received acoustical signal. In one embodiment the computer includes a personal computer programmed with a web browser and a medical data acquisition and transmission program. The medical data acquisition and transmission program can be downloaded from an Internet site accessed using the web browser.

The system of the present invention can also be defined without limitation as to type of data, such as to comprise: a plurality of initial user sites, each of the initial user sites having a data generating source and a computer connected to receive signals from the data generating source and to access the Internet; and an Internet site addressable from each of the plurality of initial user sites such that each initial user site can access a data acquisition and transmission program through the Internet site to enable the respective computer to process received signals from the respective data generating source and transmit responsive signals over the Internet. Each initial user site preferably can transmit simultaneously over the Internet to one or more recipient sites. Also, the receiving computer at a recipient site can receive and display in real time the signals from one or a multiple number of initial user sites.

A method of generating and transferring medical data in accordance with an aspect of the present invention comprises: transducing directly from a patient a human body function or condition into a first signal; converting at the site of the patient the first signal into a second signal adapted for transmission over the Internet; and transmitting the second signal over the Internet to a recipient. In one implementation the method further comprises performing the transducing, converting, and transmitting contemporaneously; and contemporaneously therewith generating at the recipient a display in response to the transmitted second signal, wherein the display is a real-time representation of the transduced human body function or condition.

A method of generating and transferring data in accordance with the present invention comprises: accessing an Internet site from a computer where a data generating source is located; downloading to the computer from the accessed Internet site a data acquisition and transmission program; and operating the computer with the downloaded data acquisition and transmission program such that the computer receives signals from the data generating source, processes the received signals, and transmits data signals onto the Internet in response thereto. In particular implementations, the downloaded program may or may not operate unless the computer is connected to the specific web site on the Internet from which the program was obtained.

A method of the present invention for generating medical data representative of a biological function or condition of an individual comprises:

(a) accessing an Internet site with a personal computer located with the individual, wherein the personal computer is programmed with a conventional operating program;

(b) downloading from the accessed Internet site to the personal computer a medical data acquisition program automatically operable with the conventional operating program;

(c) generating an acoustical signal in response to the biological function or condition of the individual;

(d) receiving the acoustical signal in a microphone near the individual and converting with the microphone the received acoustical signal into an analog electric signal;

(e) communicating the analog electric signal from the microphone to an analog to digital conversion circuit of the personal computer and converting thereby the analog electric signal to a digital electric signal;

(f) processing the digital electric signal in the personal computer under control of the medical data acquisition program; and (g) displaying to the individual, through the personal computer, a representation of the individual's biological function or condition in response to which the acoustical signal was generated.

As a step (h), responsive data can be transmitted over the Internet to other sites for storage and review. From such other site or sites, for example, data can then be transmitted over a paging or other wireless network to a physician, for example. In a preferred embodiment, at least steps (c) through (h) are performed together in real time.

Still another definition of a method of monitoring biological functions and conditions of a plurality of patients in accordance with the present invention comprises: distributing to each patient at least one sensor to detect at least one biological function or condition of the patient; and maintaining a medical data acquisition and transmission program at an Internet site accessible by the patients such that the patients can use, from computers at the locations of the patients, the medical data acquisition and transmission program to control their respective computers to receive and process signals from the patients' respective sensors and to transmit medical data onto the Internet in response thereto. This method can further comprise distributing to a plurality of physicians receivers (with or without transmitting capability) for receiving at least portions of the medical data transmitted over the Internet. It can still further comprise providing a combination Internet receiving and paging or other wireless communication network transmitting site to receive the medical data transmitted on the Internet and to transmit received medical data to at least one respective physician's receiver through the wireless network. The method can also comprise marking each sensor with indicia defining the address of the Internet site.

Therefore, from the foregoing, it is a general object of the present invention to provide a novel and improved system and method for generating and transferring medical and other data. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 5 illustrates one implementation for a patient site.

FIG. 6 is a general flow diagram for the use and operation of the implementations of FIGS. 2–5.

FIG. 7 is a more detailed block diagram of the patient site depicted in FIG. 5.

DETAILED DESCRIPTION OF THE INVENTION

Figure 1:
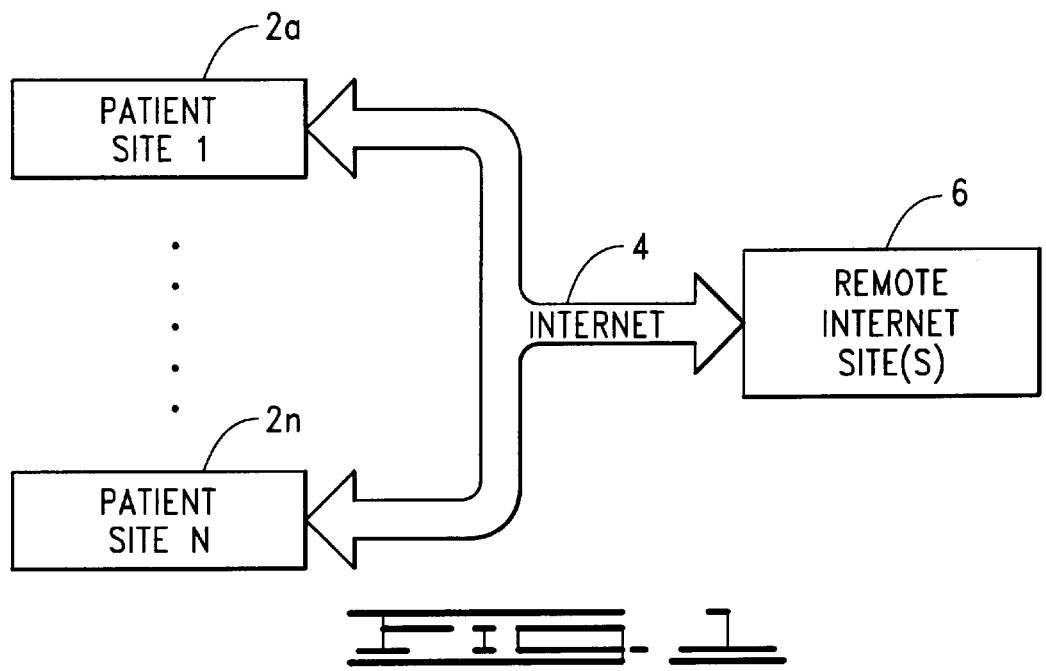
FIG. 1 is a block diagram illustrating one configuration of a system of the present invention.

A general representation of the system of the present invention as applied to one example of medical data acquisition and transmission is illustrated in FIG. 1. The present invention also can be used for generating and transferring other data that can be processed in the manner described below.

Although only one patient site need be present, typically there will be a plurality of patient sites 2a–2n (the term "patient" as used herein is not limited to someone who is ill or who is necessarily under a medical provider's care; it simply refers to an individual using the present invention in the medical context). These sites are wherever the patient (or, more broadly, initial user or simply some data generating source) is and has access to a computer and communication network, which is specifically illustrated as including the Internet 4 in the drawings and in the remainder of the following description of the present invention (the term "Internet" as used herein encompasses the global computer network commonly known by that name, any functional part of it suitable for use in the present invention (e.g., the World Wide Web), and any other suitable global computer network capable of providing the communication link of the present invention). Also connected to the Internet 4 is at least one remote site 6 with which the patient sites 2a–2n can communicate.

Figure 2:
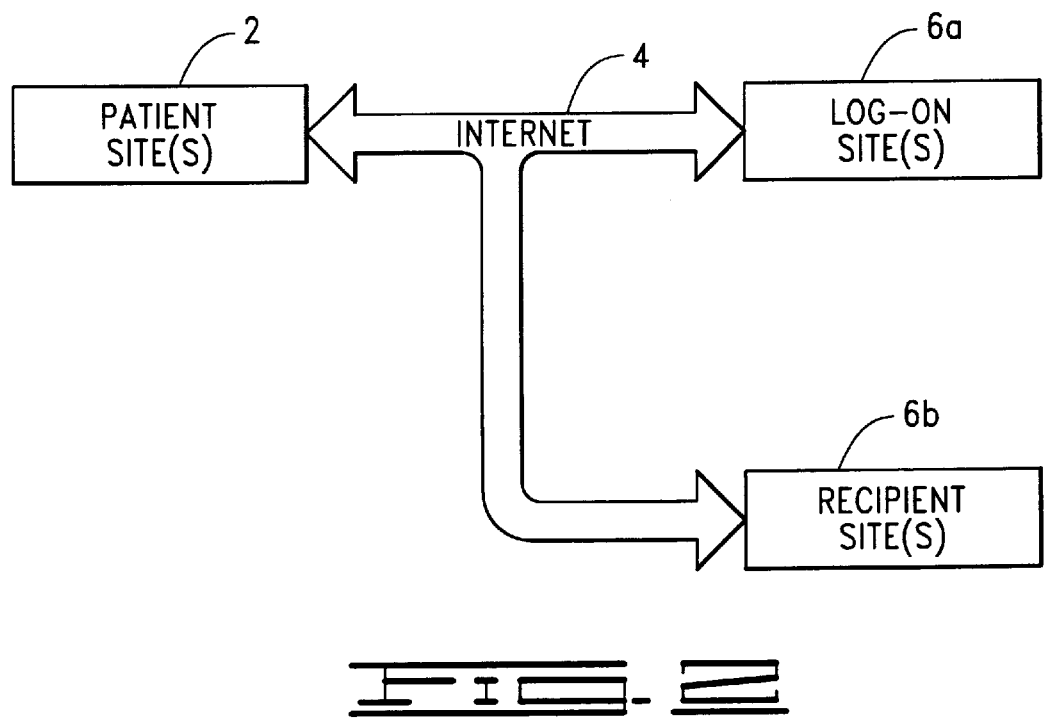
FIG. 2 is a block diagram illustrating one variation of the FIG. 1 configuration wherein a patient site accesses a log-on site to acquire a software program necessary to provide medical data to a recipient site.

The remote Internet site(s) 6 can be embodied in various manners; however, two particular types of the preferred embodiment are represented in FIG. 2. One or more log-on sites 6a are addressed by a patient at his or her site entering the log-on site's address. Such a log-on site 6a is the only site a patient need explicitly address from the respective patient site 2.

Although the foregoing is the only explicit address a patient need enter, other remote sites can be accessed, such as illustrated by recipient sites 6b in FIG. 2. In preferred embodiments, such sites are automatically addressed when data is to be sent from a patient site 2 to an end user. This can occur through a log-on site 6a, but in the illustrated embodiment of FIG. 2 there are physically and functionally distinct recipient Internet sites.

A further overview of the foregoing will be described with reference to FIGS. 3–6. A more detailed explanation will then be given with reference to FIGS. 7–10.

Figure 3:
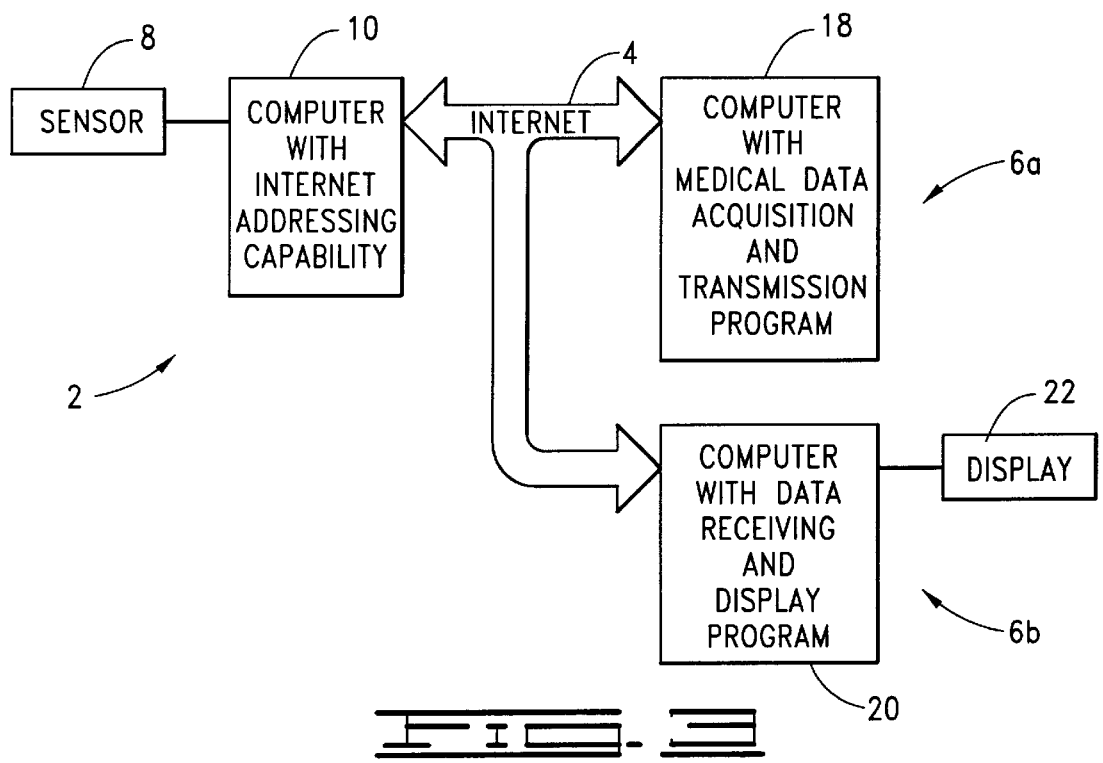
FIG. 3 is a block diagram illustrating one implementation of the system depicted in FIG. 2.

Referring to FIG. 3, a patient site 2 includes means for sensing a biological function or condition (more broadly, a data generating source; for example, a device that responds to some ambient parameter by generating a signal adaptable for use by a computer as described herein). It also includes means, communicating with the means for sensing, for transferring a response to the sensed biological function or condition over the Internet. The means for sensing includes at least one sensor 8 suitable for sensing a function or condition of the body of the respective patient. The means for transferring includes a computer 10 connected to receive signals from the one or more sensors 8 and to access the Internet 4.

In a particular implementation, the sensor 8 includes a hand-held device that is inexpensive and simple to use. As illustrated in FIG. 5, the sensor 8 includes a heart monitor that provides an audible output signal in response to the sensed biological function or condition, which in this example is the patient's heart activity. The patient can hold this device against his or her chest by hand, this can be done by another person, or the device can be attached to the chest or held by an elastic strap (for example). The sensor 8 of this implementation in FIG. 5 includes a hand-held transducer that converts energy from an adjacent beating heart of a patient 12 into an acoustical signal. The acoustical signal can be detected by a microphone 14 connected to the conventional microphone jack of a personal computer 16 implementing the computer 10. The term "personal computer" as used in this specification and claims encompasses all types of computers conventionally referred to by that name regardless of size designation (e.g., desktop, laptop, notebook, hand-held, palmtop, etc.). Non-limiting examples of sensors are those capable of providing outputs responsive to (1) changes of electrical potential occurring during the heartbeat to provide ECG data, or (2) brain waves to provide EEG data, or (3) variations in the size of an organ or limb and in the amount of blood present or passing through it to provide plethysmograph data, or (4) galvanic skin resistance.

It is to be noted that any particular sensor 8 merely needs to provide some signal suitable for inputting to the computer 10 (thus "data" of the present invention includes anything represented by such signal). The microphone 14 is used in the embodiment of FIG. 5 to convert the acoustical signal of this embodiment into a corresponding analog electric signal used by the personal computer 16. The sensor 8 can be a type that provides an electric signal output directly to the personal computer 16, for example.

The personal computer 16 in the FIG. 5 implementation is connected to the microphone 14 and includes circuits and programs to access the Internet 4 and to transfer a representation of the sensor's output signal over the Internet 4 to a selected Internet site in response to input to the personal computer 16 from the microphone 14. That is, the personal computer 16 transfers over the Internet 4 data representative of the electric signal received either from the microphone or other device, such as the sensor 8 itself, into the personal computer 16. The personal computer 16 need be programmed initially only with conventional programs sufficient to enable the patient or other user at the patient site to access the Internet 4 through the personal computer 16. This programming can include a conventional web browser. At some point in the use of the personal computer 16, it is also programmed with a medical data (or other specific type of data as used for other embodiments) acquisition and transmission program (in broader terms, simply a data acquisition and transmission program). In the preferred embodiment, this program is downloaded into the personal computer 16 from the log-on site 6a using the web browser. The program can be in any suitable form, such as in the form of an application "plug-in," a "Java applet," or in a preferred particular implementation an "ActiveX control." The personal computer 16 connects to the Internet 4 by any suitable communication link (e.g., telephone line, television cable).

The circuitry and programming of the personal computer 16 also ultimately are sufficient to provide it with the capability to read the input port receiving the signal from the microphone 14 or other input device, to process the input signal, to access the recipient Internet site to which data is to be transferred, and to send the data to the recipient site over the Internet.

Referring to FIG. 3 again, the log-on site 6a in this embodiment includes a computer 18 having the medical data acquisition and transmission program stored for downloading to a patient site 2. That is, the log-on site 6 of this implementation is an Internet site addressable from each of the plurality of patient sites such that each patient site can access the medical data acquisition and transmission program through the Internet site to enable the respective computer 10 (e.g., personal computer 16) at the respective patient site to process received signals from a patient sensor connected to it and to transmit responsive signals over the Internet 4.

The log-on site 6 can be implemented in any suitable manner. For example, it can be provided by an existing Internet service provider which the computer at a patient site accesses when the patient initially logs onto the Internet.

Still referring to FIG. 3, the recipient site 6b includes a computer 20 programmed to receive data and display it through a display 22 (e.g., a monitor or printer). In the implementation of FIG. 3, the computer 20 receives the transferred response over the Internet and directly communicates the information via the display 22. For example, the computer 20 can be located at a medical facility and connected to communicate with the Internet. Such computer is programmed to receive the response transferred over the Internet and to provide a visible representation of the sensed biological function or condition.

Figure 4:
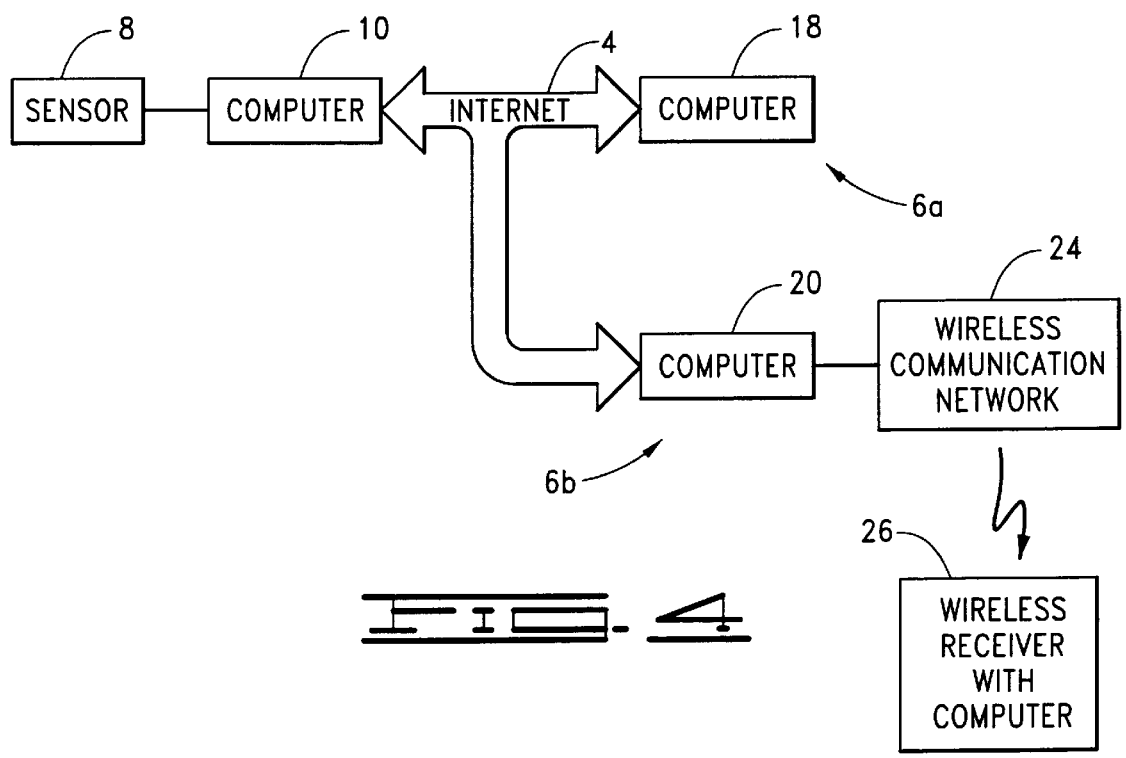
FIG. 4 is a block diagram illustrating another implementation of the system depicted in FIG. 2.

Another implementation of a recipient site 6b is illustrated in FIG. 4. In this implementation, the recipient site 6b functions as an intermediary between a patient site and an end user of the data. As shown in FIG. 4, the recipient site 6b still includes the computer 20, but which is additionally programmed to transfer the data to something other than the display 22. In FIG. 4, the computer 20 is programmed to communicate the data to a wireless network 24 (but other communication techniques can be used in other embodiments) that sends the data through its system to a wireless data receiver and computer combination 26. The wireless system is one that can provide data transmission (e.g., digital phone systems, such as GSM or CDMA which provide data transmission; two-way paging systems; one-way paging systems). This type of transfer can occur in accordance with the known technology described in the patents cited in the background explanation set forth above, which are incorporated herein by reference. In this implementation, the recipient computer 20 can be located at a data communication service provider facility. This computer 20 is connected to communicate with the Internet 4, and it is programmed to receive at least part of the responsive signals transmitted over the Internet and to transmit in response thereto end user signals from the recipient computer 20 to an end user. The end user signals are a representation of the human body function or condition (or other data) as initially sensed by the sensor 8.

Figure 8:
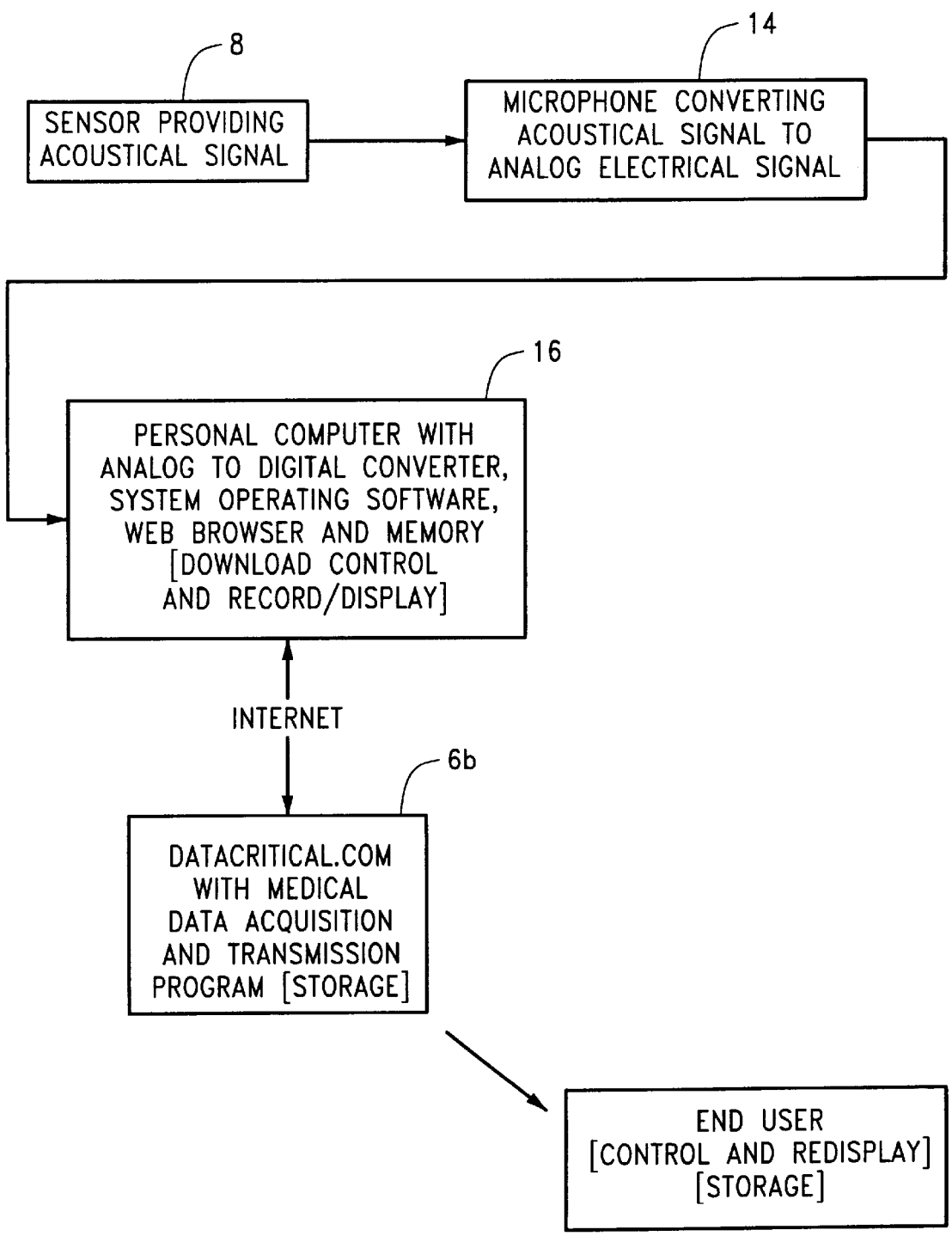
FIG. 8 illustrates a particular implementation of a system of the present invention including at least one patient site of the type shown in FIG. 7.

As mentioned above, the log-on site 6a and the recipient site 6b can be combined such that a single site provides both the medical data acquisition and transmission program to be downloaded to the patient site and also the programming necessary to receive data and directly display it or transfer it by other means to an end user. This is illustrated in FIG. 8 which is described below.

The method of the present invention for the foregoing embodiments is now described with reference to FIG. 6. Using the computer 10 (e.g., personal computer 16) where the patient is located, the Internet site having the medical data acquisition and transmission program is accessed from the respective patient's site. Access occurs by the computer 10 at the patient site 2 running its web browser or otherwise gaining access to the Internet 4. Once Internet access has been gained, the computer 10 accesses the known log-on site where the medical data acquisition and transmission program is located. This can be the site through which Internet access is gained, or the site containing the medical data acquisition and transmission program can be different from the Internet portal.

When the appropriate site has been accessed, identification information (e.g., name, password) is entered (e.g., manually by the patient or automatically by preprogramming the patient's computer 10) to enable the computer 10 at the patient site 2 to select and download the medical data acquisition and transmission program. When the appropriate information has been given to the log-on site 6a in the illustrated embodiments of FIGS. 3 and 4, the medical data acquisition and transmission program downloads to, or otherwise becomes accessible for use by, the computer 10 at the patient site 2.

The medical data acquisition and transmission program preferably downloads in active mode so that it is ready to perform the functions at the patient site 2 without the patient having to perform functions other than manipulating the sensor to sense the biological function or condition to be transmitted to the computer 10 at the patient site. In the implementation of FIG. 5, the patient 12 holds the heart monitor 8 against his or her chest. The heart monitor 8 responds to the beating heart by generating corresponding acoustical signals transmitted to the microphone 14. The microphone 14 converts the signals to analog electric signals communicated to the personal computer 16 programmed with the downloaded medical data acquisition and transmission program. In using the medical data acquisition and transmission program, the personal computer 16 receives the signals, processes the received signals, and transmits medical data signals onto the Internet 4 in response.

Transmitting over the Internet 4 to a recipient site 6b includes accessing a second Internet site from the computer 10 and transmitting patient data over the Internet to the accessed second Internet site 6b, both under control of the medical data acquisition and transmission program used by the computer 10.

In addition to the foregoing which is illustrated in FIG. 6, the method of the present invention can further comprise receiving, over the Internet, the transmitted medical data signals at a recipient site. As explained above, this can be any suitable site, such as a medical facility or a data communication service provider facility. The former would typically be an end user of the data whereas the latter would typically be an intermediary that transfers the data onto an end user. As explained above with reference to FIG. 4, such could include transmitting, from the data communication server provider facility to an end user, end user signals responsive to the received medical data signals. In FIG. 4, this includes transmitting the medical data signals through the wireless data network 24.

When the data is received by the end user, a display is generated in response to a received signal. The display is a representation of the transduced human body function or condition. In the example of a heart monitor implementing the sensor 8, the display can be a waveform corresponding to the detected heart beat energy. This display can be by way of a computer monitor or printer or other display device.

The method of the present invention can also be defined as comprising distributing by any suitable means (e.g., through direct mail, at physicians' offices) at least one sensor to each patient. For example, this includes distributing to a plurality of patients respective portable heart monitoring devices that the respective patients can hold against their chests without assistance. Each sensor can be marked with indicia defining the address of the Internet site of the log-on site 6a. In the preferred embodiments of FIGS. 3 and 4, this can include the World Wide Web address for the respective log-on site 6a that one or more of the patients is to access to download the medical data acquisition and transmission program.

The method further comprises maintaining the medical data acquisition and transmission program at the Internet site which is accessible by the patients such that the patients can use the medical data acquisition and transmission program to control their respective computers to receive and process signals from the patients' respective sensors and to transmit medical data onto the Internet in response. Use of the program is made by accessing the Internet site using a web browser program or other suitable programming loaded on the computer at the location of the patient.

Maintaining the medical data acquisition and transmission program includes storing the program in a computer at the Internet site 6a for FIGS. 3 and 4. The method can further comprise storing in the computer at the Internet site a database of potential recipients of the medical data, wherein the database is also accessible by each patient such that each patient can identify from the potential recipients at least one selected recipient to receive the medical data for that patient.

One way of getting the information to the end users is to distribute to a plurality of physicians receivers for receiving at least portions of the medical data transmitted over the Internet. The receivers (which may also have transmitting capability can include pagers connected to palmtop computers such as referred to in the patents mentioned in the background portion of this specification and incorporated herein by reference.

A more detailed explanation of the foregoing will next be given with reference to FIGS. 7–10.

FIG. 7 shows a particular implementation of the components generally identified in FIG. 5. This includes the sensor 8, the microphone 14 and the personal computer 16. The sensor 8 provides an acoustical signal in simultaneous response to a biological function or condition, namely a beating heart in the illustrated implementation. The microphone 14 is located with the sensor 8 to receive the acoustical signal as the signal is provided from the sensor 8. The personal computer 16 is connected to the microphone and is adapted to transfer over the Internet, in real-time response to the microphone receiving the acoustical signal, electric signals representative of the received acoustical signal.

The sensor 8 of the FIG. 7 implementation includes a device 30 that converts the beating heart energy into electric signals. This can be by conventional electrocardiogram (ECG) electrodes as represented in FIG. 7 or other suitable device (e.g., a suitable piezoelectric device). The electric signals generated by the device 30 are amplified through an amplifier 32. The output of the amplifier 32 is processed through a voltage to frequency converter 34 to provide an alternating current signal that drives a speaker 36 to emit the acoustical signal directed toward the microphone 14.

The microphone 14 converts the acoustical signal into an analog electric signal conducted through a connected microphone jack 38 of the personal computer 16. The microphone jack 38 connects to the input of an analog to digital converter circuit 40 in the personal computer 16. The circuit 40 interfaces the microphone to the computer by converting the analog signal from the microphone 14 to a digital signal that can be used by a microprocessor circuit 42. The microprocessor circuit 42 is connected to a mouse 44, a keyboard 46, and a display 48. The microprocessor circuit 42 also communicates with an Internet connection 50, such as a coupling to a telephone line (e.g., a modem).

The analog to digital converter circuit 40 preferably provides at least eight-bit resolution and samples at 8,000 or more samples per second; this can be implemented with conventional technology, one example of which is a SOUND BLASTER brand sound card from Creative Labs. The microprocessor circuit 42 is also conventional, but preferably has a microprocessor nominally rated at least 20 megahertz. It also includes suitable memory for program storage and processing functions (e.g., typically both read only memory and random access memory). The programming of such memory is also conventional prior to loading the medical data acquisition and transmission program referred to above. This conventional programming can include, for example, a Windows operating system and a compatible web browser, such as Microsoft's INTERNET EXPLORER program or Netscape's NAVIGATOR program. Thus, the foregoing, and the other components illustrated in FIG. 7, can be implemented with conventional devices.

With the equipment of FIG. 7, shown in simplified blocks in FIG. 8, a patient at the site of the sensor 8, microphone 14 and personal computer 16 uses the web browser stored in the personal computer 16 to log onto the Internet. Typically this occurs through whatever Internet service provider the patient uses. Non-limiting examples include America On-Line and AT&T Worldnet. Once logged onto the Internet through his or her Internet service provider, the patient types in the address of the Internet site containing the medical data acquisition and transmission program if it is not available at the Internet service provider site. For example, for the illustration in FIG. 8, the patient enters the address "http//www.datacritical.com". The home page of datacritical.com appears on the display 48 of the personal computer 16. Through this home page, the patient downloads or otherwise accesses the medical data acquisition and transmission program. In one example, the datacritical.com home page contains a link that the patient selects to go to a page from which the program is downloaded. This linked page includes patient identification entry spaces, such as calling for the patient's unique password, to enable only a registered patient to download the program if such registry is desired to permit someone to download the program.

An example of a medical data acquisition and transmission program that is downloaded to the patient's computer 16 is appended at the end of this specification. The program can be of any suitable language and type to enable the implementation of the present invention; however, non-limiting examples include a program in ActiveX, or Java, or a plug-in module. Preferably the program is downloaded in an active mode so that the patient does not need to do anything to actuate the program to receive the medical data and to process it for display locally or transmission onto the Internet.

With the downloaded program running, an acoustical signal is generated at the patient site in response to the biological function or condition of the individual being monitored. This includes the heart monitor for the illustration of FIGS. 7 and 8. The acoustical signal is received in the microphone 14 near the individual. The microphone 14 converts the acoustical signal into an analog electric signal. The analog electric signal is communicated from the microphone 14 to the analog to digital conversion circuit 40 where it is converted to a digital electric signal. The digital electric signal is processed in the microprocessor circuit 42 of the personal computer 16 under control of the medical data acquisition and transmission program that has been downloaded and is actively running. The program can then display to the individual, through the display 48 of the personal computer 16, a representation of the individual's biological function or condition in response to which the acoustical signal was generated. The medical data acquisition and transmission program can also transmit the data onto the Internet. In the illustration of FIG. 8, the data is transmitted to datacritical.com where it can be stored in a searchable database and transmitted to an end user. Preferably the transmission to the end user occurs contemporaneously with the foregoing steps so that there is real-time transmission of the data from the time the biological function or condition of the individual was sensed to the time it is received by the end user. Thus, once the program has been downloaded into the personal computer 16, preferably the subsequent steps from sensing the condition through display to the individual at the patient's site or transmission to an end user are performed together in real time. The data downloaded to the end user can also be stored in the end user's computer for later retrieval. Thus, the medical information derived from the sensing activity can be useful both for clinical purposes by an end user medical care provider as well as for providing self-knowledge benefits for the patient, such as in monitoring his or her own biological functions or conditions.

Figure 9:
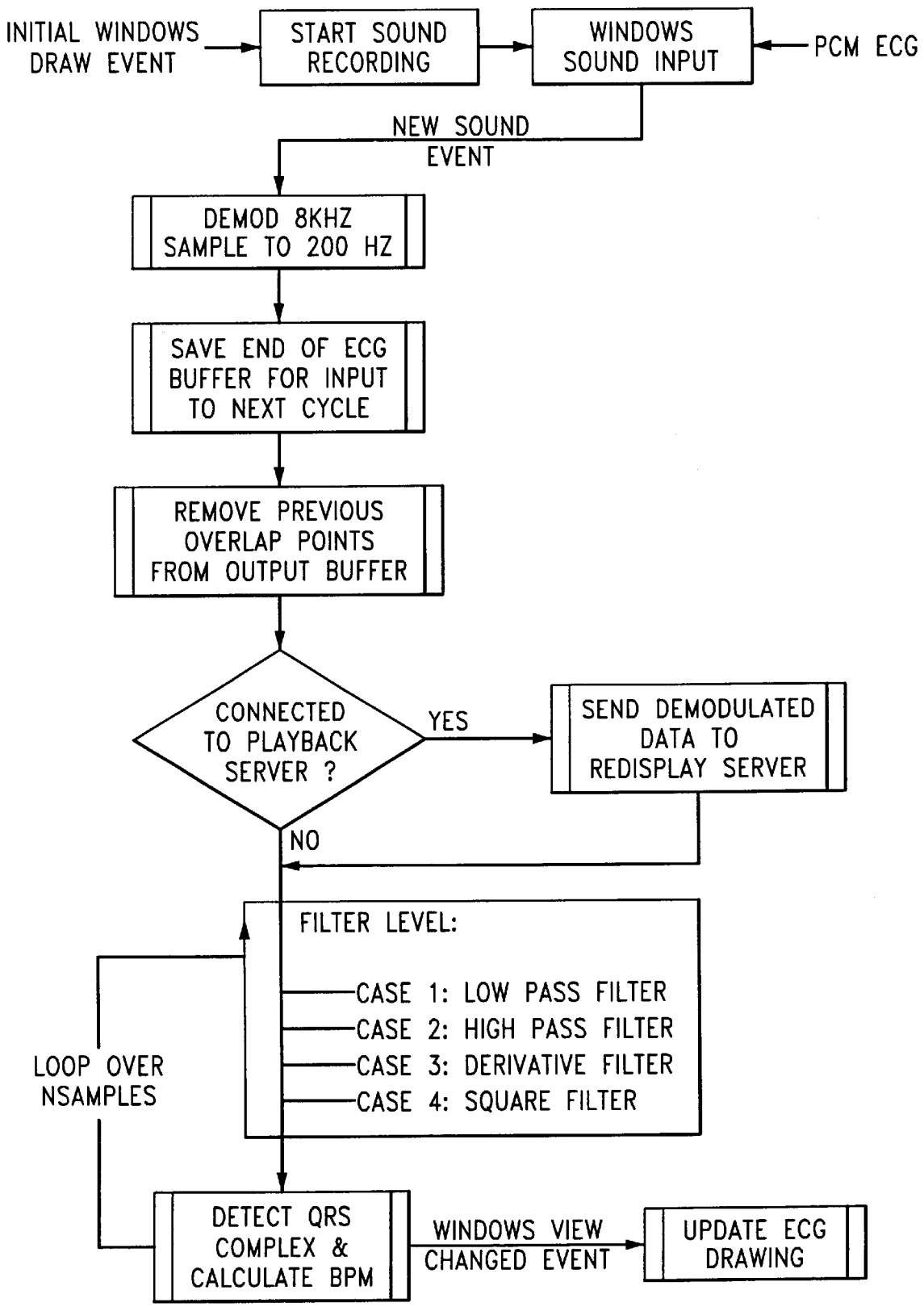
FIG. 9 is a flow diagram for a medical data acquisition and transmission program for the FIG. 8 system.

A flow diagram of a preferred embodiment of the medical data acquisition and transmission program downloaded to the personal computer 16 is illustrated in FIG. 9, and the source code is listed at the end of this specification before the claims. The program is an ActiveX control in combination with an HTML page which collects, filters and displays a user's ECG waveform and heart rate. When the control is embedded in a web page (e.g., at datacritical.com in the FIG. 8 illustration), it is downloaded to the user's personal computer 16 and configured to record ECG data from the microphone 14 connected to the personal computer 16 and to display the ECG waveform in the browser window of the personal computer 16. Configuration of the control is achieved via HTML "Param" tags. The control is embedded in an HTML page via the "Object" tag-this tells the browser to load the control. After the "Object" tag, and the name of the control, come the "Param" tags which provide values for named parameters of the control. For example, in the appended program listing there is a parameter called "Microphone_Not_Server," and the Param statement looks like:

<PARAM NAME="Microphone_Not_Server" VALUE="1">

This statement initializes the control to listen for data at the microphone.

The browser-loaded control can also stream, across the Internet, demodulated ECG data to a redisplay server at a recipient site if one is available. The redisplay server also contains a control program (see FIG. 10 and program listing) that processes the forwarded ECG data.

When the program of FIG. 9 operates in the personal computer 16 at a patient's site, the data source in this implementation referring to FIGS. 7–10 is an 8 kilohertz pulse code modulated (PCM) ECG signal received from the analog to digital converter circuit 40 in response to the acoustical signal sensed by the microphone 14. When the control is contained in a redisplay server, the data source is demodulated ECG data that has been sent from the personal computer 16 over the Internet to the redisplay server (or from the personal computer to datacritical.com and then to the redisplay server via the Internet or a paging network, for example).

In the flow diagram of FIG. 9, once the control has been downloaded to the user's personal computer, it is configured via an HTML "Param" tag to collect data from the microphone as input through the analog to digital converter circuit 40 as explained above. The control may also be configured to connect to a redisplay server via another "Param" tag in the manner described above. The control then receives a "draw yourself" event from Windows. The first time this event is received, the control starts listening for data on the microphone.

Upon receiving data from the microphone, the control demodulates the data from 8 kilohertz pulse code modulated to 200 hertz ECG samples. If a redisplay server is specified, the control streams the new, demodulated samples to the server over the Internet.

Once the ECG data has been demodulated, it is filtered based upon the filtering level set in a "Param" tag on the web page. Filtering levels are as listed in FIG. 9 (low pass filter, high pass filter, derivative filter, square filter).

The most recent two seconds worth of filtered data is then scanned for QRS complexes to determine the user's heart rate in beats per minute. The software fires a Windows "my view has changed" event, which causes Windows to call the control's "OnDraw" routine such that "OnDraw" updates the screen 48 of the personal computer 16 with the latest ECG waveform and heart rate.

Figure 10:
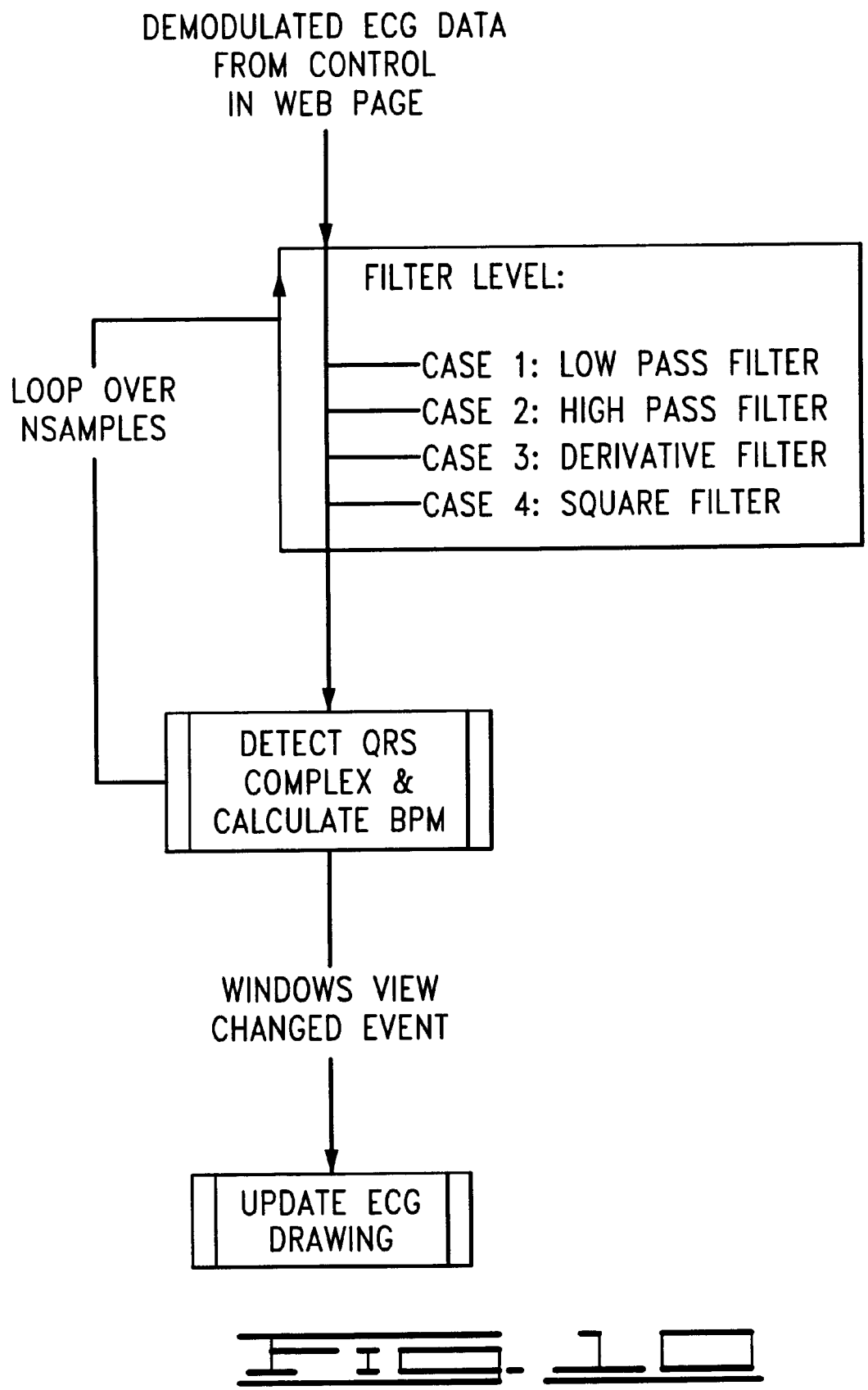
FIG. 10 is a flow diagram for displaying data at a recipient Internet site remote from the patient's site of the FIG. 8 system.

Referring to FIG. 10, in a redisplay server, the program enables the server to listen at a known port for incoming demodulated ECG samples from a remote site. When samples are received, the server passes them to the control's filtering routine as described above. The same chain of events then occurs: the samples are filtered, QRS detection is executed, and the waveform is updated to the remote server's window.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. A system for generating and transferring medical data, comprising:

means for sensing a biological function or condition, wherein the means for sensing provides an audible output signal in response to the sensed biological function or condition; and means, communicating with the means for sensing, for transferring a response to the sensed biological function or condition over the Internet, wherein the means for transferring includes:
a microphone to respond to the audible output signal;
an electrical circuit connected to the microphone to convert an analog signal from the microphone to a digital signal; and
a microprocessor circuit connected to the electrical circuit and programmed to access the Internet and to transfer in real time a representation of the audible output signal over the Internet to a selected Internet site in response to the digital signal.

2. A system for generating and transferring medical data, comprising:
a sensor used by a human user to sense a function or condition of the user's body,
a personal computer located with the sensor and having a microphone connector and analog to digital conversion means communicated with the sensor such that a digital processing circuit of the personal computer receives from the analog to digital conversion means a digital electric signal derived from an analog electric signal received through the microphone connector in response to the user's body function or condition sensed by the sensor, wherein the personal computer is programmed to transfer data representative of the received digital electric signal over a computer communication network contemporaneously with the sensor sensing the user's body function or condition; and
a recipient computer located at a medical facility and connected to communicate with the computer communication network, wherein the recipient computer is programmed to receive the data transferred over the computer communication network and to provide a visible representation of the sensed body function or condition and to store the data in a searchable database; and wherein:
the sensor generates an acoustical signal; and
the system further comprises a microphone connected to the microphone connector to provide the analog electric signal in response to the acoustical signal.

3. A system for generating and transferring medical data, comprising:
a sensor used by a human user to sense a function or condition of the user's body;
a personal computer located with the sensor and having a microphone connector and analog to digital conversion means communicated with the sensor such that a digital processing circuit of the personal computer receives from the analog to digital conversion means a digital electric signal derived from an analog electric signal received through the microphone connector in response to the user's body function or condition sensed by the sensor, wherein the personal computer is programmed to transfer data representative of the received digital electric signal over a computer communication network contemporaneously with the sensor sensing the user's body function or condition, and
a recipient computer located at a data communication service provider facility and connected to communicate with the computer communication network, wherein the recipient computer is programed to receive the data transferred over the computer communication network and to transmit in response thereto another signal to an end user; and wherein:
the sensor generates an acoustical signal; and
the system further comprises a microphone connected to the microphone connector to provide the analog electric signal in response to the acoustical signal.

4. A system for generating and transferring medical data, comprising:
a sensor used by a human user to sense a function or condition of the user's body; and
a personal computer located with the sensor and having a microphone connector and analog to digital conversion means communicated with the sensor such that a digital processing circuit of the personal computer receives from the analog to digital conversion means a digital electric signal derived from an analog electric signal received through the microphone connector in response to the user's body function or condition sensed by the sensor, wherein the personal computer is programmed to transfer data representative of the received digital electric signal over a computer communication network contemporaneously with the sensor sensing the user's body function or condition; and wherein:
the sensor generates an acoustical signal; and
the system further comprises a microphone connected to the microphone connector to provide the analog electric signal in response to the acoustical signal.

5. A system for generating and transferring medical data in real time, comprising:
a sensor to provide an acoustical signal in simultaneous response to a biological function or condition;
a microphone, located with the sensor, to receive the acoustical signal as the acoustical signal is provided from the sensor; and
a computer connected to the microphone and adapted to transfer over the Internet, in real-time response to the microphone receiving the acoustical signal, electric signals representative of the received acoustical signal.

6. A system as defined in claim 5, wherein the sensor includes a hand-held transducer that converts energy from an adjacent beating heart of a patient into the acoustical signal.

7. A system as defined in claim 6, wherein the computer is a personal computer including: a microprocessor circuit that has a microprocessor which operates at a nominal speed of at least twenty megahertz, and a microphone interface circuit connected to the microphone and the microprocessor circuit.

8. A system as defined in claim 7, wherein the personal computer is programmed with a web browser and a medical data acquisition and transmission program.

9. A system as defined in claim 8, wherein the medical data acquisition and transmission program is downloaded into the personal computer from an Internet site accessed using the web browser.

10. A system as defined in claim 5, wherein the computer is programmed with a web browser and a medical data acquisition and transmission program.

11. A system as defined in claim 10, wherein the medical data acquisition and transmission program is from an Internet site accessed using the web browser.

12. A method of generating and transferring medical data, comprising:
transducing directly from a patient a human body function or condition into a first signal;
contemporaneously converting at the site of the patient the first signal into a second signal adapted for transmission over the Internet; and
transmitting the second signal over the Internet to a recipient in real time with the steps of transducing and converting;

wherein transducing includes the patient manipulating a portable sensor adjacent the patient's body such that the sensor senses the human body function or condition and generates the first signal in response thereto; and wherein the sensor generates an acoustical signal as the first signal.

13. A method as defined in claim 12, wherein converting the first signal into a second signal includes receiving the acoustical signal at a microphone having an output connected to a computer adapted for processing an output signal of the microphone to provide the second signal in response thereto.

14. A method as defined in claim 13, wherein converting the first signal into the second signal further includes downloading into the computer a medical data acquisition and transmission program from the recipient.

15. A method as defined in claim 13, wherein converting the first signal into the second signal further includes downloading into the computer, from an Internet site different from the recipient, a medical data acquisition and transmission program.

16. A method of generating and transferring medical data, comprising:

transducing directly from a patient a human body function or condition into a first signal;

converting at the site of the patient the first signal into a second signal adapted for transmission over the Internet; and transmitting the second signal over the Internet to a recipient;

wherein converting the first signal into the second signal includes downloading into a computer a medical data acquisition and transmission program from the recipient.

17. A method of generating and transferring medical data, comprising:

transducing directly from a patient a human body function or condition into an acoustical signal;

converting using, a microphone and conventional patient-usable personal computer at the site of the patient, the acoustical signal into an electrical signal adapted for transmission over the Internet;

transmitting, using the conventional patient-usable personal computer, the electrical signal over the Internet to a recipient; and performing the transducing, converting, and transmitting contemporaneously, and contemporaneously therewith generating at the recipient a display in response to the transmitted second signal, wherein the display is a real-time representation of the transduced human body function or condition.

18. A method of generating and transferring medical data, comprising:

transducing directly from a patient a human body function or condition into a first signal;

converting at the site of the patient the first signal into a second signal adapted for transmission over the Internet:

transmitting the second signal over the Internet to a recipient;

transmitting a medical data signal from the recipient to a second recipient in response to the first-mentioned recipient receiving the transmitted second signal; and performing the transducing, converting and two transmitting steps contemporaneously, and contemporaneously therewith generating at the second recipient a display in response to the transmitted medical data signal, wherein the display is a real-time representation of the transduced human body function or condition.

19. A method of generating and transferring medical data, comprising:

transducing directly from a patient a human body function or condition into an acoustical signal;

converting, using a microphone and conventional patient-usable personal computer at the site of the patient, the acoustical signal into an electrical signal adapted for transmission over the Internet;

transmitting, using the conventional patient-usable personal computer, the electrical signal over the Internet to a recipient; and transmitting a medical data signal from the recipient to a second recipient in response to the first-mentioned recipient receiving the transmitted second signal;

wherein the medical data signal is transmitted through a paging network.

20. A method of generating and transferring medical data, comprising:

generating an acoustical signal in response to a human body function or condition, wherein generating an acoustical signal includes a patient holding a portable heart monitor against the patient's chest where the patient's heartbeat energy is detected such that the portable heart monitor generates the acoustical signal in response to the heartbeat energy;

converting the acoustical signal into a corresponding electric signal;

processing the electric signal in a conventional patient-usable personal computer to provide a data signal; and transmitting the data signal onto the Internet from the computer.

21. A method as defined in claim 20, wherein converting the acoustical signal includes receiving the acoustical signal in a microphone located near the patient and connected to the computer.

22. A method of generating and transferring medical data, comprising steps of:

(a) accessing a site on a computer communication network with a personal computer located with a patient;

(b) downloading from the accessed site to the personal computer a medical data acquisition and transmission program;

(c) holding a heart monitor against a patient and converting with the heart monitor energy from the beating heart of the patient into acoustical signals;

(d) receiving the acoustical signals in a microphone near the heart monitor and converting with the microphone the received acoustical signals into analog electric signals;

(e) communicating the analog electric signals from the microphone to an analog to digital conversion circuit of the personal computer and converting thereby the analog electric signals to digital electric signals; and (f) processing the digital electric signals in the personal computer under control of the medical data acquisition and transmission program;

wherein at least steps (c) through (f) are performed together in real time.

23. A method as defined in claim 22, further comprising accessing from the personal computer a second site on the computer communication network, and transmitting patient heart data over the computer communication network to the accessed second site in real-time response to the processed digital electric signals, both under control of the medical data acquisition and transmission program in the personal computer.

24. A method as defined in claim 23, further comprising contemporaneously transmitting, from a computer at the second site, the patient heart data over a wireless communication network to a physician.

25. A method of monitoring biological functions and conditions of a plurality of patients, comprising:
distributing to each patient at least one sensor to detect at least one biological function or condition of the patient;
maintaining a medical data acquisition and transmission program at an Internet site accessible by the patients such that the patients can use, from computers at the locations of the patients, the medical data acquisition and transmission program to control their respective computers to receive and process signals from the patients' respective sensors and to transmit medical data onto the Internet in response thereto; and
distributing to a plurality of physicians receivers for receiving at least portions of the medical data transmitted over the Internet.

26. A method as defined in claim 25, further comprising providing a combination Internet receiving and wireless network data transmitting site to receive the medical data transmitted on the Internet and to transmit received medical data to at least one respective physician's receiver through a wireless network.

27. A method of monitoring biological functions and conditions of a plurality of patients, comprising:
distributing to each patient at least one sensor to detect at least one biological function or condition of the patient;
maintaining a medical data acquisition and transmission program at an Internet site accessible by the patients such that the patients can use, from computers at the locations of the patients, the medical data acquisition and transmission program to control their respective computers to receive and process signals from the patients' respective sensors and to transmit medical data onto the Internet in response thereto; and
marking each sensor with indicia defining the address of the Internet site.

28. A method of monitoring biological functions and conditions of a plurality of patients, comprising:
distributing to each patient at least one sensor to detect at least one biological function or condition of the patient; and
maintaining a medical data acquisition and transmission program at an Internet site accessible by the patients such that the patients can use, from computers at the locations of the patients, the medical data acquisition and transmission program to control their respective computers to receive and process signals from the patients' respective sensors and to transmit medical data onto the Internet in response thereto;
wherein maintaining the medical data acquisition and transmission program includes storing the program in a computer at the Internet site and wherein the method further comprises storing a database of potential recipients of the medical data, the database also accessible by each patient such that each patient can identify from the potential recipients at least one selected recipient to receive the medical data for that patient.

29. A method as defined in claim 28, further comprising communicating, to a respective patient's at least one selected recipient, the medical data transmitted onto the Internet for that patient.

30. A remote heart monitoring method, comprising:
distributing to each of a plurality of patients a respective portable heart monitoring device that the respective patient can hold against his or her chest without assistance;
maintaining a medical data acquisition and transmission program at a first Internet site known to the patients such that each patient can access, using a web browser program of a computer at the location of the patient, the medical data acquisition and transmission program to control the computer to receive and process signals from the patient's respective heart monitoring device and to transmit medical data onto the Internet in response thereto and in response to automatic operation of the medical data acquisition and transmission program;
receiving the transmitted medical data at a second Internet site; and
communicating, from a computer at the second Internet site, respective portions of the medical data to respective end users of the medical data.

31. A method as defined in claim 30, wherein communicating respective portions of the medical data includes transmitting the respective portions over a paging network to hand-held computers of respective end user medical providers.

32. A method as defined in claim 31, further comprising marking each heart monitoring device with the web address of the first Internet site.

33. A method as defined in claim 30, further comprising marking each heart monitoring device with the web address of the first Internet site.

34. A method of generating medical data representative of a biological function or condition of an individual, comprising:
(a) accessing an Internet site with a personal computer located with the individual, wherein the personal computer is programmed with a conventional operating program;
(b) downloading from the accessed Internet site to the personal computer a medical data acquisition program automatically operable with the conventional operating program;
(c) generating an acoustical signal in response to the biological function or condition of the individual;
(d) receiving the acoustical signal in a microphone near the individual and converting with the microphone the received acoustical signal into an analog electric signal;
(e) communicating the analog electric signal from the microphone to an analog to digital conversion circuit of the personal computer and converting thereby the analog electric signal to a digital electric signal;
(f) processing the digital electric signal in the personal computer under control of the medical data acquisition program; and (g) displaying to the individual, through the personal computer, a representation of the individual's biological function or condition in response to which the acoustical signal was generated.

35. A method as defined in claim 34, wherein at least steps (c) through (g) are performed together in real time.

36. A method as defined in claim 35, further comprising in real time with at least steps (c) through (g), transmitting from the personal computer over the Internet data responsive to the processed digital electric signal.

37. A method as defined in claim 34, further comprising in real time with at least steps (c) through (g), transmitting from the personal computer over the Internet data responsive to the processed digital electric signal.

* * * * *

UNITED STATES PATENT AND TRADEMARK OFFICE
CERTIFICATE OF CORRECTION

PATENT NO. : 6,264,614 B1
DATED : July 24, 2001
INVENTOR(S) : David E. Albert, Carl J. Rieger, Mac L. Reiter and Rik Slaven It is certified that error appears in the above-identified patent and that said Letters Patent is hereby corrected as shown below:

Title page,
First line under OTHER PUBLICATIONS, delete "Lahti" and insert -- Lathi -- therefor; and delete "Commincation" and insert -- Communication -- therefor.
U.S. PATENT DOCUMENTS, second column, third line from bottom, delete "Lliff" and insert -- Iliff -- therefor.

Column 13,
Line 60, delete "programed" and insert -- programmed -- therefor.

Column 15,
Line 40, delete "converting using," and insert -- converting, using -- therefor.

Signed and Sealed this

Twenty-sixth Day of March, 2002

JAMES E. ROGAN
*Director of the United States Patent and Trademark Office*

*Attest:*

*Attesting Officer*